United States Patent [19]

Koller

[11] Patent Number: 5,665,119
[45] Date of Patent: Sep. 9, 1997

[54] FILLING MEMBER MADE FROM METAL FOR BONE CAVITIES

[75] Inventor: Hansjörg Koller, Winterthur, Switzerland

[73] Assignee: Sulzer Medizinaltechnik AG, Switzerland

[21] Appl. No.: 251,862

[22] Filed: May 31, 1994

[30]   Foreign Application Priority Data

Jul. 1, 1993 [EP] European Pat. Off. ............. 93810466

[51] Int. Cl.$^6$ .................................................. A61F 2/28
[52] U.S. Cl. ........................... 623/16; 140/107; 623/66
[58] Field of Search .......................... 623/11, 16, 18, 623/20, 21, 66, 1; 606/86, 92–95, 154; 140/71 C, 107; 502/325; 15/229.11, 229.12

[56]   References Cited

U.S. PATENT DOCUMENTS

| | | | |
|---|---|---|---|
| 3,906,550 | 9/1975 | Rostoker et al. | 623/16 |
| 4,343,335 | 8/1982 | Kobayashi et al. | 140/70 C |
| 4,464,482 | 8/1984 | Bird et al. | 502/345 |
| 4,693,721 | 9/1987 | Ducheyne | 623/16 |
| 4,745,914 | 5/1988 | Frey et al. | 606/86 |
| 5,197,978 | 3/1993 | Hess | 623/1 |
| 5,397,359 | 3/1995 | Mittelmeier et al. | 623/16 |
| 5,480,437 | 1/1996 | Draenert | 623/16 |

FOREIGN PATENT DOCUMENTS

| | | |
|---|---|---|
| 0 220 427 | 5/1987 | European Pat. Off. . |
| 0 338 976 | 10/1989 | European Pat. Off. . |
| 0 366 018 | 5/1990 | European Pat. Off. . |
| 0 526 682 | 2/1993 | European Pat. Off. . |
| 29 10 627 | 9/1980 | Germany . |

*Primary Examiner*—Robert A. Clarke
*Attorney, Agent, or Firm*—Townsend and Townsend and Crew LLP

[57]   ABSTRACT

A tubular member (1) made from wire, preferably titanium wire, which is manufactured on a round knitting machine, is inserted into the cavity (3c) of a pressing tool (2) having a pressing mold (3b) and die (3a). The tubular member (1) is plastically deformed by the die (3a) introduced into the cavity (3c), so that the member (1) assumes the shape predetermined by the pressing mold (3b), and thus is transformed to produce a member (4) which can be inserted as a filling member (4) into bone cavities, for example as a medullary space barrier.

15 Claims, 1 Drawing Sheet

FILLING MEMBER MADE FROM METAL FOR BONE CAVITIES

BACKGROUND OF THE INVENTION

The invention relates to a filling member made from metal for bone cavities. The invention also relates to a process for the manufacture of such filling members.

During operations on bones, in particular during the implantation of hip joints, it may be necessary in a bone cavity to insert a filling member to provide the bone with an additional support, or to delimit the bone cavity, for example in relation to the medullary space. The filling member has to meet high requirements. Thus the filling member has to be biologically compatible and have the property that during and after the operation no individual fragments become detached from the filling member and become deposited anywhere in the body in an uncontrolled manner. U.S. Pat. No. 3,906,550 discloses a filling member which is made from short, randomly curved, metal fibers, which were baked in a sintering process to form a porous filling member. A material very well tolerated by the body is titanium; however it is extremely exacting to work. If titanium is heated during the working process for forming, for example in a sintering process, there is the danger of embrittlement. In a filling member worked with such a forming process there is thus the danger of individual fragments becoming detached. Heating during the forming operation may be avoided by a metal-cutting production. However in this case there is the danger that extremely small chips are formed.

SUMMARY OF THE INVENTION

It is therefore an object of the invention is to produce a filling member for bone cavities which has improved properties with respect to the detachment of individual fragments, by which its porosity can be affected.

The filling member of the present invention is made from a knitted fabric, whereby it can be shaped by plastically deforming the knitted fabric.

The advantages of the invention are regarded as being that individual fragments no longer become detached from the filing member. The filling member is normally made from a knitted fabric which is manufactured with a single wire or a few wires. The plastic deformation of the knitted fabric produces a cohesive unit of knitted loops so that the individual loops can no longer become detached. The plastic deformation of the knitted fabric is advantageously to be performed so that the wires plastically deform but do not break. After deformation the filling member has pores. The porosity of the filling member and the strength of the filling member may be varied within wide limits via the pressing force and also the choice of the wire diameter or of the wire cross section. If the filling member is to be made from pure titanium, corresponding wires made from pure titanium are to be used. One advantage is regarded as being that to shape the filling member made from pure titanium neither heating nor a metal-cutting manufacturing process is required. A further advantage is regarded as being that by shaping the filling member by means of plastic deformation, a plurality of possible shapes can be produced, in particular if the process of the plastic deformation is performed in several individual steps.

The invention is described below by means of an exemplified embodiment.

DESCRIPTION OF THE PREFERRED EMBODIMENTS

Knitted fabrics are fabrics which are manufactured from one or more thread systems by loop formation on knitting or hosiery machines. FIG. 1b shows a detail of a knitted fabric 2d, the loops 2a of which are made from a wire 2. The size of the loops 2a and thus the bending radius of the wire 2 may vary within wide limits during manufacture. Knitted fabrics 2d in particular possess in the width direction, i.e. in the horizontal direction with respect to FIG. 1b, a high elongation and elasticity. A large pore volume is also produced by the loop structure.

Figure 1A:
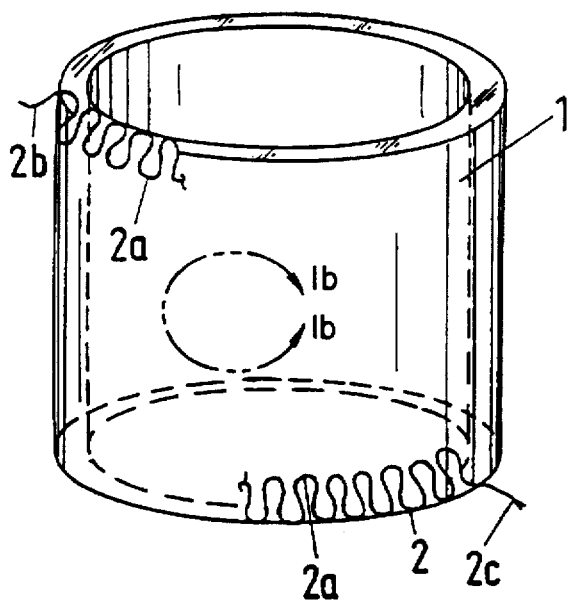
FIG. 1a shows a cylindrical knitted fabric.
Figure 1B:
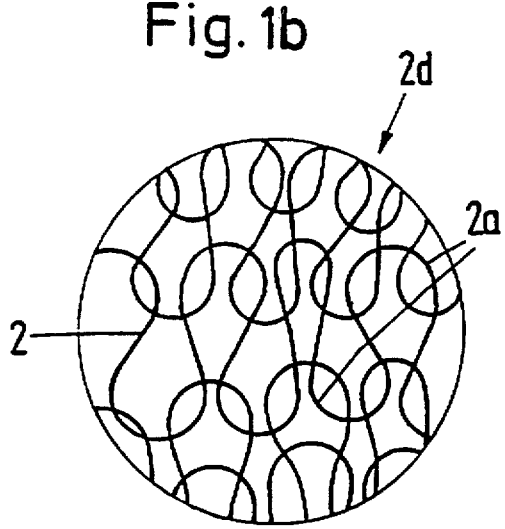
FIG. 1b shows a detailed view of the thread pattern in the knitted fabric.
Figure 2A:
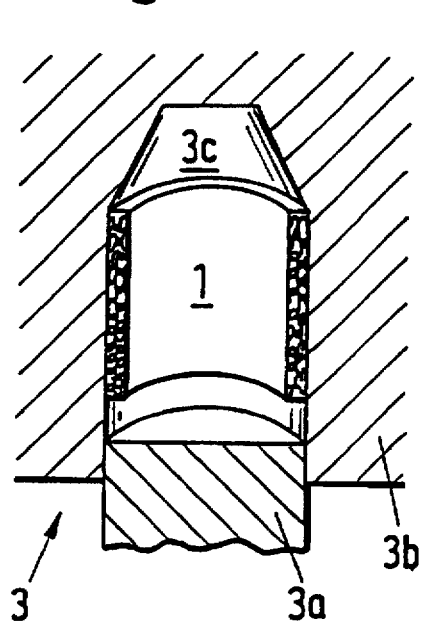
FIG. 2a shows a device for the shaping before pressing.
Figure 2B:
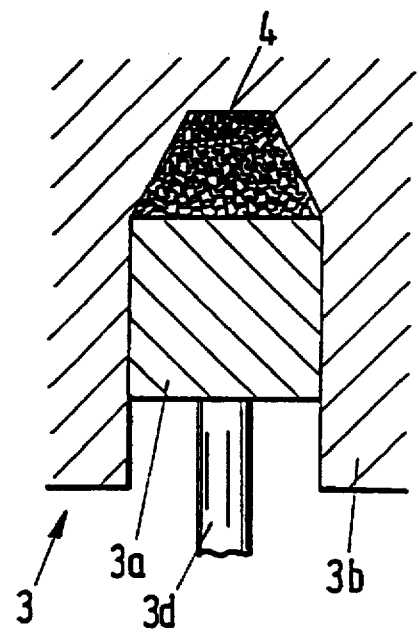
FIG. 2b shows a device for shaping after pressing.
Figure 2C:
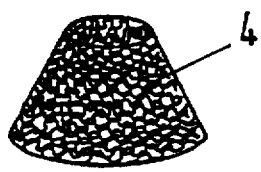
FIG. 2c shows a filling member.

FIG. 1a illustrates a metallic filling member in the form of a tubular member 1 made of wire 2, preferably titanium wire, which is manufactured on a circular knitting machine. In the present exemplified embodiment the whole fabric 1 consists of a single wire 2, having two wire ends 2b, 2c. The knitted fabric has relatively large loops and is relatively loose so that the wire 2 can be worked by knitting and a blank 1 in the form of a hollow cylinder can be produced. For pure titanium a wire diameter of between 0.1 mm and 0.8 mm has proved to be particularly advantageous. In a further process step, which is represented in FIGS. 2a–2c, a filling member 4 is formed out of the blank 1 by pressing operations. FIG. 2a shows a pressing tool 3 having pressing mold 3b, die 3a and cavity 3c. The tubular member 1 is inserted in the cavity 3c and, as represented in FIG. 2b, is plastically deformed by the die 3a entering the cavity 3c, so that the member 1 assumes the shape predetermined by the pressing mold 3b, and thus is transformed into a member 4. The wire ends 2b, 2c are advantageously inserted into the member 1 before the reforming of the member 1, so that the ends come to lie in the interior of the transformed member 4 after the reforming operation. FIG. 2c shows a member 4 in the shape of a truncated cone, which can be inserted as a filling member 4 into bone cavities, for example as a medullary space barrier. The plastic reformation of the tubular member 1 may of course occur over several steps and with various tools, so that a filling member 4, the shape of which is suitable, for example, for insertion into bone cavities, is only produced after several operating steps. The porosity of the filling member 4 is of course also influenced by the plastic deformation. The manufacturing process permits a large variety of shapes for the filling member 4 with varying porosity. Thus the loop fabric 1 can be knitted in very different ways, and also as a flat, plane fabric which can also have recesses. The knitted fabric can be produced with several threads or wires, in which case they may also have varying diameters or cross sections.

What is claimed is:

1. A metallic filling member for a bone cavity of a given shape comprising a fabric knitted from a titanium metal wire and is compressed by being plastically deformed into a three-dimensional shape which is substantially smaller that its original dimension and corresponds to the given shape of the bone cavity.

2. The filling member according to claim 1 wherein the titanium metal wire has a diameter in a range of between 0.1 mm and 0.8 mm.

3. The filling member according to claim 1, wherein the filling member has a shape selected from a group consisting of cylindrical, conical, truncated conical and cubical shapes.

4. The metallic filling member according to claim 1 wherein the three-dimensionally shaped wire fabric has an outer surface, and wherein the first and second ends are disposed inside the outer surface.

5. The filling member according to claim 1 wherein the metal wire comprises a single metal wire.

6. The filling member according to claim 1 wherein portions of the wire intermediate its ends are mutually interconnected loops which define the only interconnection between the wire portions.

7. A metallic filling member for a bone cavity comprising a single titanium metallic wire having first and second ends, knitted into a fabric establishing numerous points of contact between portions of the titanium metallic wire intermediate its ends, and plastically deformed by compression into a three-dimensional shape which is substantially smaller that its original dimension for insertion as a three-dimensional shape wire fabric into the bone cavity, wherein the three-dimensional shape wire fabric has an outer surface, and wherein the first and second ends are disposed inside the outer surface.

8. The filling member according to claim 7, wherein the titanium metal wire is made from pure titanium.

9. A method for producing a metallic filling member for a bone cavity comprising the steps of providing a metal wire, knitting the metal wire to form a tubular knitted metal wire fabric having an original dimension, and three-dimensionally plastically deforming the knitted metal wire fabric by compression into a shape which is substantially smaller than the original dimension of the tubular knitted metal wire fabric and corresponds to the shape of the bone cavity.

10. The process according to claim 9 wherein the step of knitting comprises the step of knitting a single metal wire into the knitted metal wire fabric.

11. The process according to claim 9 wherein the metal wire has ends, and including the step of positioning the ends of the metal wire on an interior of the tubular knitted metal wire fabric.

12. A process for producing a metallic filling member for placement in a bone cavity comprising the steps of providing a single metal wire having wire ends, looping the single metal wire a multiplicity of times about itself to form a fabric defining loops of looped metal wire which mutually connect respective portions of the single metal wire, thereafter three-dimensionally plastically deforming by compression the looped metal wire to give a three-dimensionally deformed wire which is substantially smaller than its original dimension and corresponds to a shape of the bone cavity, and positioning the wire ends so that they are located inside an exterior surface defined by the three-dimensionally deformed wire.

13. A method for producing a metallic filling member for a bone cavity comprising the steps of providing a metal wire having ends, knitting the metal wire to form a knitted metal wire fabric, three-dimensionally plastically deforming the knitted metal wire fabric by compression into a shape which is substantially smaller than its original dimension and corresponds to a shape of the bone cavity, and positioning the ends of the wire on an interior of the knitted metal wire fabric.

14. The process according to claim 13 wherein the step of knitting comprises the step of knitting the wire into a tubular knitted fabric.

15. The process according to claim 13 wherein the step of positioning is performed prior to the step of deforming.

* * * * *